(12) United States Patent
Clarence-Smith

(10) Patent No.: US 12,390,454 B2
(45) Date of Patent: Aug. 19, 2025

(54) USE AND COMPOSITION FOR PROTECTION AGAINST ORGANOPHOSPHORUS POISONING

(71) Applicant: Kathleen E. Clarence-Smith, Washington, DC (US)

(72) Inventor: Kathleen E. Clarence-Smith, Washington, DC (US)

( * ) Notice: Subject to any disclaimer, the term of this patent is extended or adjusted under 35 U.S.C. 154(b) by 0 days.

(21) Appl. No.: 17/895,946

(22) Filed: Aug. 25, 2022

(65) Prior Publication Data
US 2022/0409599 A1 Dec. 29, 2022

Related U.S. Application Data

(62) Division of application No. 16/612,876, filed as application No. PCT/US2018/038189 on Jun. 19, 2018, now Pat. No. 11,439,630.

(60) Provisional application No. 62/539,784, filed on Aug. 1, 2017, provisional application No. 62/521,667, filed on Jun. 19, 2017.

(51) Int. Cl.
| | | |
|---|---|---|
| A61K 31/4425 | (2006.01) | |
| A61K 31/24 | (2006.01) | |
| A61K 31/407 | (2006.01) | |
| A61K 31/4178 | (2006.01) | |
| A61K 31/438 | (2006.01) | |
| A61K 31/5377 | (2006.01) | |
| A61P 1/08 | (2006.01) | |

(52) U.S. Cl.
CPC .......... *A61K 31/4425* (2013.01); *A61K 31/24* (2013.01); *A61K 31/407* (2013.01); *A61K 31/4178* (2013.01); *A61K 31/438* (2013.01); *A61K 31/5377* (2013.01); *A61P 1/08* (2018.01)

(58) Field of Classification Search
CPC .................................................. A61K 31/4425
See application file for complete search history.

(56) References Cited

U.S. PATENT DOCUMENTS

| | | | |
|---|---|---|---|
| 5,916,903 A | 6/1999 | Viner | |
| 2014/0294926 A1* | 10/2014 | Chang | A61K 9/1272 424/178.1 |
| 2016/0143890 A1* | 5/2016 | Chase | A61K 31/473 514/299 |

OTHER PUBLICATIONS

Capacio et al., Interaction of Pyridostigmine with the 5-HT(3) Receptor Antagonist Ondansetron in Guinea Pigs, Proceedings of the Medical Defense Bioscience Review, May 10-13, 1993, pp. 799-809, vol. 2.*
Pohanka et al., Inhibitors of acetylcholinesterase and butyrylcholinesterase meet immunity, Int J Mol Sci. Jun. 2, 2014;15(6):9809-25.*
Hesketh et al., Efficacy of the neurokinin-1 receptor antagonist rolapitant in preventing nausea and vomiting in patients receiving carboplatin-based chemotherapy, Cancer, vol. 122, Issue15, Aug. 1, 2016, pp. 2418-2425.*
BR. Capacio, et al., "Interaction of Pyridostigmine with the 5-HT(3) Receptor Antagonist Ondansetron in Guinea Pigs", Proceedings of the Medical Defense Bioscience Review, May 10-13, 1993, pp. 799-809, vol. 2.
Miroslav Pohanka, "Inhibitors of Acetylcholinesterase and Butyrylcholinesterase Meet Immunity", International Journal of Molecular Sciences, Jun. 2, 2014, pp. 9809-9825, vol. 15.
Diana Romero, "Rolapitant—a new and safer antiemetic agent", Nature Reviews Clinical Oncology, Aug. 25, 2015, pp. 562, vol. 12.
International Search Report for PCT/US2018/038189 dated Sep. 7, 2018 [PCT/ISA/210].

* cited by examiner

*Primary Examiner* — Svetlana M Ivanova
(74) *Attorney, Agent, or Firm* — Sughrue Mion, PLLC

(57) ABSTRACT

The present invention relates to compositions comprising an antiemetic, particularly including 5-HT3 antagonist and/or NK-1 antagonist antiemetics, in combination with a choline esterase inhibitor such as an acetylcholine esterase inhibitor and/or a butyrylcholine esterase inhibitor, and methods of using the composition to provide improved protection of subjects at risk of organophosphorus poisoning, or, for the treatment, prevention, or alleviation/reduction of toxicity from an organophosphorus compound, by enabling the use of a highly protective daily dose of the choline esterase inhibitor without the typical adverse effects.

23 Claims, No Drawings

USE AND COMPOSITION FOR PROTECTION AGAINST ORGANOPHOSPHORUS POISONING

RELATED APPLICATIONS

This application is a divisional of U.S. application Ser. No. 16/612,876, filed on Nov. 12, 2019 (allowed), which is a National Stage of International Application No. PCT/US2018/038189, filed on Jun. 19, 2018, which claims the benefit of U.S. Provisional Patent Application Ser. No. 62/521,667, filed Jun. 19, 2017, and U.S. Provisional Patent Application Ser. No. 62/539,784, filed Aug. 1, 2017, the disclosures of which are incorporated herein in their entirety by reference.

FIELD OF THE INVENTION

The present invention pertains to the field of preventive antidotal therapy of organophosphorus (OP) poisoning in humans and mammals exposed to or at risk of exposure to OP compounds, a composition comprising an antiemetic selected from 5-HT3 and NK-1 antagonists, in combination with an acetylcholine esterase inhibitor or a butyrylcholine esterase inhibitor or a choline esterase inhibitor; and a method of using such compostions for preventing, treating, or alleviating an effect of an OP compound. The invention safely enables the efficacy of preventive antidotal therapy against OP poisoning.

Definitions

"5-HT3 antagonist": an antagonist of the 5-HT3 receptor subtype-1.
"ACh": Acetylcholine.
"AChE": Acetylcholine esterase.
"AChEI": Acetylcholine esterase inhibitor.
"AE(s)": Adverse Effect(s).
"BuChE": Butyrylcholine esterase.
"BuChEI": Butyrylcholine esterase inhibitor.
"ChE": Choline esterase.
"ChEI": Choline esterase inhibitor.
"CNS": Central Nervous System.
"ER": Extended Release of the active ingredient from a composition.
"GI": Gastro-Intestinal.
"IM": Intramuscular.
"IR": Immediate Release of the active ingredient from a composition.
"IV": Intravenous.
"NK-1 antagonist": neurokinin receptor subtype-1 ($NK_1$-antagonist), also referred to
as NK-1 receptor inhibitor or simply NK-1-antagonist.
"OP": Organophophorus.
"TTS": Transdermal Therapeutic System.
"Antiemetic": may include, but is not limited to, a 5-HT3 antagonist, a NK-1 receptor antagonist, a dopamine antagonist, a histamine H1 receptor antagonist, a cannabinoid, a benzodiazepine, and an anticholinergic.

BACKGROUND OF THE INVENTION

The organophosphorus compounds, soman (pinacolyl methylfluorophosphonate), sarin, VX (venomous agent X or ethyl ([2-{bis(propan-2-yl)amino]ethyl}sulfanyl)(methyl) phosphinate), and tabun (ethyl dimethylamidocyanophosphate), referred to as nerve agents, are among the most lethal chemical weapons ever developed (Coupland and Leins, 2005). Nerve agents are chemically related to OP insecticides such as, but not limited to, chlorpyrifos-oxon, diazinon-oxon, and paraoxon. Intoxication with OP insecticides represents a major public-health concern worldwide (Pohanca, 2014; Karalliedde and Snanayake, 2005; Buckley et al. 2004). Most of the acute toxicity of OP compounds results from the irreversible inhibition of acetylcholinesterase (AChE), the enzyme that inactivates the neurotransmitter acetylcholine (ACh) (Bajgar, 2004). However, OP compounds also inactivate butyrylcholinesterase (BuChE), an enzyme that scavenges OP compounds as well as inactivating ACh. Inactivation of BuChE by OP compounds further contributes to toxicity.

OP compounds readily cross the blood-brain-barrier. Consequently, irreversible inhibition of AChE leads to accumulation of fatal amounts of ACh in the periphery and in the brain. In the periphery, ACh accumulation leads to severe muscle fasciculations and subsequent weakness, diarrhea, hypotension, bronchoconstriction, bradycardia, profuse secretions, and miosis. Central nervous system-related effects include anxiety, restlessness, confusion, ataxia, tremors, seizures, cardiorespiratory paralysis, and coma (Albuquerque et al. 2006).

Current therapeutic strategies to decrease OP toxicity include cholinergic receptor antagonists to reduce the muscarinic syndrome, oximes to reactivate OP-inhibited AChE, anticonvulsants to control OP-triggered seizures, and butyrylcholinesterases to act as OP scavengers (Doctor et al. 1991).

Among other therapies, certain AChE (and BuChE) inhibitors can be protective of these enzymes by temporarily binding to the enzymes and thus preventing the OP compounds from long term (days) binding to the enzymes. The enzymes are able to function again after a relatively short time (hours) when said certain AChE (and BuChE) inhibitors clear the receptor sites and OP is no longer present. For example, pyridostigmine bromide, a quaternary carbamate that does not appreciably cross the blood-brain-barrier, reversibly inhibits AChE and BuChE with similar potencies, and has been approved for use among military personnel who are under threat of exposure to nerve agents. Neostigmine is also a quaternary carbamate that does not appreciably cross the blood-brain-barrier, and reversibly inhibits AChE and BuChE with similar potencies. Rivastigmine and physostigmine, two carbamates that cross the blood-brain-barrier, also reversibly inhibit both AChE and BuChE with similar potencies, and should afford better protection against OP intoxication (Triggle et al. 1998; Pohanka, 2014) as they protect AChE and BuChE not only in the periphery, but also in the brain. Physostigmine also interacts directly with, and potentiates nicotininc ACh receptors, a disadvantage in a situation where the receptors are exposed to abnormally high amounts of acetylcholine in the synaptic cleft. However, physostigmine has the major advantage, when administered intravenously by bolus, of reaching peak enzyme inhibition (>70%) within 2 minutes of administration, and can therefore be useful for allowing for very rapid protection against OP poisoning (Walter et al, 1995).

Rivastigmine, (S)—N-Ethyl-N-methyl-3-[1-(dimethylamino)ethyl]-phenyl carbamate, inhibits AChE and BuChE in a pseudo-irreversible manner (Darreh-Shori and Soininen, 2010). Slow elimination of rivastigmine because of the covalent bond in the active site of the enzymes is an advantage over other ChE inhibitors. The effect of rivastigmine lasts until the rivastigmine moiety spontaneously splits from the ChE active site by a decarbonylation process (Tayeb et al. 2012; Bartolucci et al. 2012).

Unfortunately, dose-limiting AEs, consisting mainly of nausea, vomiting, and diarrhea, preclude the use of higher and therefore more effective doses of compounds that inhibit both AChE and BuChE, such as pyridostigmine, neostigmine, rivastigmine, and physostigmine.

Pyridostigmine bromide, iodide or methylsulfate is commonly used for the treatment of myasthenia gravis. Pyridostigmine bromide (Mestinon®) was approved by the US Food and Drug Administration (FDA) in 2003 as a pretreatment in humans against the lethal effects of the irreversible nerve agent soman. Studies in primates (Haigh et al, 2010) showed that AChE activity in red blood cells was inhibited by 18% and 50% respectively by a low (12.5 µg/kg) and a high (39.5 µg/kg) pyridostigmine dose. By contrast soman inhibited 98% of AChE activity in red blood cells (and, in a chemical warfare context, soman would disrupt AChE activity for days while pyridostigmine would inhibit AChE activity only for a few hours while protecting the binding sites from OP compounds). Clearly, a higher dose of pyridostigmine could further and more efficiently protect against soman poisoning, but dose-limiting gastro-intestinal side effects preclude the use of higher doses.

Neostigmine is commercially available as a brand or generic drug, for example as oral Prostigmin®, consisting of tablets comprising 15 mg neostigmine bromide and vials for parenteral injection comprising 0.5 mg of neostigmine methylsulfate, a 15 mg of neostigmine bromide oral dose being equivalent to 0.5 mg of neostigmine methylsulfate parenteral dose.

A neostigmine bromide slow release preparation which can be taken once every day for treating myasthenia gravis is described in CN 102258492, the contents of which are incorporated herein in their entirety for reference.

Neostigmine is also described in combination with some plant extracts according to traditional Chinese medicine (CN 102552381), for treating myasthenia gravis.

A process for the synthesis of neostigmine iodide and neostigmine methylsulfate is disclosed in RU 2010130899, the contents of which are incorporated herein in their entirety by reference.

Neostigmine methylsulfate has been disclosed as a remedy for eye diseases, in an eye drop preparation, consisting of a neostigmine methylsulfate aqueous solution, also containing other chemicals, emulsified with an oily higher fatty acid solution obtained from olive oil and isopropyl myristate (JPS 56104814, the contents of which are incorporated herein in their entirety by reference).

Neostigmine methylsulfate has also been disclosed, in combination with naphazoline hydrochloride and chlorpheniramine maleate, for the treatment of conjunctivitis (CN 105708838, the contents of which are incorporated herein in their entirety by reference).

Physostigmine, a reversible cholinesterase inhibitor also known as eserine, was described in the early 1980s as protective against soman poisoning but based on its side effects, pyridostigmine was judged to be a preferable treatment (Xia et al, 1981). Heckert et al. (2011) showed that in guinea pigs prophylactic pretreatment with physostigmine prevented complete inhibition of AChE by soman and resulted in partial spontaneous recovery of the enzyme by de-carbamylation. More recently, a transdermal patch system containing procyclidine, an N-methyl-d-aspartate receptor antagonist possessing anticholinergic action, and physostigmine, was developed, and its prophylactic efficacy against soman intoxication was investigated (Cho et al, 2012). Male rhesus monkeys were shaved on the dorsal area, and a matrix-type patch applied, with various sizes (2×2 to 7×7 cm) for 24 or 72 h, and challenged with 2×LD$_{50}$ doses (13 µg/kg) of soman. The smallest patch size for the protection against lethality induced by soman intoxication was 3×3 cm, resulting in a blood procyclidine concentration of 10.8 ng/ml, a blood physostigmine concentration of 0.54 ng/ml, and a blood cholinesterase inhibition of 42%. The drug concentrations and enzyme inhibition rate corresponding to a diverging point of survivability were estimated to be around 7 ng/ml for procyclidine, 0.35 ng/ml for physostigmine, and 37% of enzyme inhibition.

Arcava et al. (2009), reported on the use of pretreatment with high doses of rivastigmine to protect guinea pigs against soman toxicity. Rivastigmine is a AChE inhibitor that crosses the blood-brain-barrier. It is approved as a transdermal patch and as an oral formulation for the treatment of Alzheimer's disease. However, when given alone in doses that are tolerated, rivastigmine has been reported to inhibit only approximately 20% to 30% of AChE activity in human brain (Kaasinen et al, 2002).

Dose-limiting gastro-intestinal adverse effects of all of the above-described AChEIs and BuChEIs consist mainly of nausea, vomiting, and diarrhea. As a consequence of these dose-limiting side effects, protection against nerve agents and certain insecticides and pesticides is reduced and incomplete.

Thus, the problem of providing safe, chronic pretreatment against deadly OP compounds with the approved therapeutic doses for pyridostigmine, neostigmine, physostigmine, and rivastigmine remains unsolved.

SUMMARY OF THE INVENTION

The present invention relates to the use of an antiemetic, and in particular, a 5-HT3 receptor antagonist and/or a NK-1 receptor antagonist, in combination with a ChEI. It has now been found that it is possible, with such a combination, to pretreat humans or other mammals that are at risk of being exposed to lethal doses of OP compounds, by enabling the safe administration of a fully protective dose of a ChE inhibitor such as pyridostigmine bromide, neostigmine, rivastigmine, or physostigmine.

In particular embodiments, it has been found that a 5-HT3 antagonist, or a NK-1 antagonist, by reducing or even abrogating the side effects of high doses of ChEIs, enables higher doses of the ChEI to be safely administered and thus enabling greater protection against OP poisoning.

In particular embodiments, the present invention provides a combination of a 5-HT3 antagonist and a NK-1 antagonist to reduce or abrogate the side effects of high doses of ChEIs, and enable higher doses of the ChEI to be safely administered and thus provide greater protection against OP poisoning.

The present invention provides a pharmaceutical composition containing an effective daily dose of an antiemetic and an effective daily dose of a choline esterase inhibitor. The antiemetic is preferably selected from a 5-HT3 antagonist and a NK-1 antagonist.

The present invention also provides a pharmaceutical composition comprising an antiemetic combination and an effective daily dose of a choline esterase inhibitor. The antimetic combination is preferably, a combination of a 5-HT3 antagonist and a NK-1 antagonist.

The 5-HT3 antagonist is present in an amount up to 10 times a pediatric or adult dose approved for the prevention of chemotherapy-induced nausea and vomiting.

The NK-1 antagonist is present in an amount up to 6 times a pediatric or adult dose approved for the prevention of chemotherapy-induced nausea and vomiting. Thus, the present invention also provides compositions and methods for alleviating/reducing or preventing OP poisoning that comprise administering to a patient in need of said treatment a combination of a 5-HT3 antagonist and/or a NK-1 antagonist, with a fully effective dose of a ChEI such as an AChE inhibitor and/or a BuChE inhibitor.

DETAILED DESCRIPTION

Other objects and advantages of the present invention will become apparent from the following detailed description together with the appended claims.

The present invention provides methods and compositions useful for safely improving the protection of humans and other mammals at risk of being exposed to OP compounds, and pre-treated with a ChE inhibitor, by chronic or recurrent administration of an antiemetic such as a 5-HT3 antagonist, an NK-1 antagonist, or combination thereof, to said humans and other mammals. The present invention also provides methods and compositions useful for safely treating, preventing, or alleviating/reducing an effect of an OP compound in humans and mammals exposed to an OP compound.

Toxicity or symptoms of toxicity following exposure to nerve agents (OP compounds) include, but are not limited to, a runny nose, coughing, tightness in the chest, difficulty breathing or shortness of breath, constriction of the pupils, blurry vision, profuse salivation, involuntary salivation, muscle twitching, seizures/convulsions, involuntary urination, involuntary defecation, lacrimate, gastrointestinal pain, nausea, vomiting, blisters and burning of the eyes and/or lungs, respiratory depression, and death.

Any of the antimetics such as 5-HT3 antagonists, NK-1 antagonists, or combinations thereof, disclosed in the literature may be used in combination with a dose of an ChEI including, but not limited to, pyridostigmine, neostigmine, physostigmine, and/or rivastigmine that maximally inhibits ChE in the periphery (pyridostigmine; neostigmine) as well as in the central nervous system (rivastigmine; physostigmine). The chronic or recurrent use of this combination increases the protection afforded by the ChEI by concurrently mitigating or even eliminating the adverse effects induced by these ChE inhibitors alone.

According to the present invention, preferably, the 5-HT3 or NK-1 antagonists used are those approved for preventing nausea and vomiting following cancer chemotherapy.

In particular, surprisingly, 5-HT3 or NK-1 antagonists, known to block nausea, vomiting, and diarrhea induced by chemotherapeutic drugs, have been shown, when administered, for 5-HT3 antagonists administered at high doses, and for NK-1 antagonists at doses in the range from 60% of recommended doses to doses higher than recommended doses, to also block the gastro-intestinal side effects of AChE inhibitors.

This finding is surprising also because to date no one thought that, by combining an effective dose of a 5-HT3 antagonist, a NK1-antagonist, or a combination thereof, with an effective dose of ChE inhibitors, it would have been possible to safely improve the protection of humans at risk of being exposed to lethal amounts of an OP compound, or to safely treat, prevent or alleviate/reduce an effect of an OP compound in humans or other mammals exposed to lethal amounts of an OP compound.

Thus, the present invention provides a method for protecting humans or other mammals at risk of OP poisoning, which comprises administering to a patient in need of said treatment an effective daily dose of an antiemetic such as a 5-HT3 antagonist, or of a NK-1 antagonist, administered orally as IR, ER, sustained release (SR) or sublingual tablets, intramuscularly, subcutaneously, or intravenously in combination with an effective daily dose of a pharmaceutically acceptable salt of pyridostigmine, neostigmine, rivastigmine, or physostigmine administered orally as IR, ER, SR or sublingual tablets, intramuscularly, subcutaneously, or intravenously. The intravenous route has the advantage of reaching effective concentrations within minutes, allowing for fast protection against an OP exposure, but has the disadvantage of a relatively short duration of action, approximating 1 to 2 hours, and therefore requiring repeat administrations.

The present invention also provides a method for protecting humans or other mammals at risk of OP poisoning, which comprises administering to a patient in need of said treatment an effective daily dose of antiemetic such as a 5-HT3 antagonist and an effective daily dose of antiemetic such as a NK-1 antagonist, administered in combination orally as IR, ER, sustained release (SR) or sublingual tablets, intramuscularly, subcutaneously, or intravenously in combination with an effective daily dose of a pharmaceutically acceptable salt of pyridostigmine, neostigmine, rivastigmine, or physostigmine administered orally as IR, ER, SR or sublingual tablets, intramuscularly, subcutaneously, or intravenously.

EMBODIMENTS

The terms "effective daily dose of 5-HT3 antagonist" and "effective daily dose of NK-1 antagonist", as used herein refer, respectively, to a dose of said 5-HT3 antagonist or to a dose of said NK-1 antagonist that is at least as high as or equal to a dose used to treat or prevent nausea and vomiting in pediatric or adult patients undergoing cancer chemotherapy according to the current protocols for said treatment. In particular preferred embodiments, a dose of said 5-HT3-antagonist is higher or greater than an effective daily dose of 5HT3-antagonist and a dose of said NK-1 antagonist is higher or greater than an effective daily dose of NK-1 antagonist.

According to particular embodiments, the invention provides pharmaceutical combinations comprising an antiemetic, where the antiemetic is a 5-HT3 antagonist or a NK-1 antagonist, at a dose that is at least as high as or equal to the pediatric or adult dose approved for the prevention of chemotherapy-induced nausea and vomiting, and an effective dose of a pharmaceutically acceptable salt of pyridostigmine, neostigmine, rivastigmine, or physostigmine. In further embodiments, the invention provides pharmaceutical combinations comprising an antiemetic, where the antiemetic is a 5-HT3 antagonist or a NK-1 antagonist, at a dose that is higher or greater than the pediatric or adult dose approved for the prevention of chemotherapy-induced nausea and vomiting, and an effective dose of a pharmaceutically acceptable salt of pyridostigmine, neostigmine, rivastigmine, or physostigmine.

According to other particular embodiments, the invention provides pharmaceutical combinations comprising a 5-HT3 antagonist and a NK-1 antagonist, each at a dose that is at least as high as or equal to the pediatric or adult dose approved for the prevention of chemotherapy-induced nausea and vomiting, and an effective dose of a pharmaceutically acceptable salt of pyridostigmine, neostigmine, rivastigmine, or physostigmine. In further embodiments, the invention provides pharmaceutical combinations comprising a 5-HT3 antagonist and a NK-1 antagonist, each at a dose that is higher or greater than the pediatric or adult dose approved for the prevention of chemotherapy-induced nausea and vomiting, and an effective dose of a pharmaceutically acceptable salt of pyridostigmine, neostigmine, rivastigmine, or physostigmine.

According to further embodiments, the invention provides an antiemetic, where the antiemetic is a 5-HT3 antagonist or a NK-1 antagonist, in pharmaceutical compositions comprising, as an active ingredient, said antiemetic in an amount at least as high as or equal to the pediatric or adult dose approved for the prevention of chemotherapy-induced nausea and vomiting, in admixture with a pharmaceutical carrier, for use for preventing or curing the adverse effects of pyridostigmine in pretreatment of OP poisoning. In alternative embodiments, the invention provides an antiemetic, where the antiemetic is a 5-HT3 antagonist or a NK-1 antagonist, in pharmaceutical compositions comprising, as an active ingredient, said antiemetic in an amount higher or greater than the pediatric or adult dose approved for the prevention of chemotherapy-induced nausea and vomiting, in admixture with a pharmaceutical carrier, for use for preventing or abrogating the adverse effects of pyridostigmine in pretreatment of OP poisoning.

According to further embodiments, the invention provides an antiemetic combination, where the antiemetic combination is a 5-HT3 antagonist and a NK-1 antagonist, in pharmaceutical compositions comprising said antiemetic combination and where the 5-HT3 antagonist and a NK-1 antagonist are each in an amount at least as high as or equal to the pediatric or adult dose approved for the prevention of chemotherapy-induced nausea and vomiting, in admixture with a pharmaceutical carrier, for use for preventing or curing the adverse effects of pyridostigmine in pretreatment of OP poisoning. In alternative embodiments, the invention provides an antiemetic combination, where the antiemetic combination is a 5-HT3 antagonist and a NK-1 antagonist, in pharmaceutical compositions comprising said antiemetic combination and where the 5-HT3 antagonist and the NK-1 antagonist are each in an amount higher or greater than the pediatric or adult dose approved for the prevention of chemotherapy-induced nausea and vomiting, in admixture with a pharmaceutical carrier, for use for preventing or abrogating the adverse effects of pyridostigmine in pretreatment of OP poisoning.

According to further embodiments, the invention includes the use of an antiemetic, where the antiemetic is a 5-HT3 antagonist or a NK-1 antagonist, for the preparation of medicaments consisting of a pharmaceutical composition comprising, as an active ingredient, said antiemetic, in an amount at least as high as or equal to the pediatric or adult dose approved for the prevention of chemotherapy-induced nausea and vomiting, in admixture with a pharmaceutical carrier, for preventing or curing the adverse effects of pyridostigmine in the pretreatment of OP poisoning. The invention also includes the use of an antiemetic, where the antiemetic is a 5-HT3 antagonist or a NK-1 antagonist for the preparation of medicaments consisting of a pharmaceutical composition comprising, as an active ingredient, said antiemetic, in an amount higher or greater than the pediatric or adult dose approved for the prevention of chemotherapy-induced nausea and vomiting, in admixture with a pharmaceutical carrier, for preventing or curing the adverse effects of pyridostigmine in the pretreatment of OP poisoning.

According to further embodiments, the invention includes the use of an antiemetic combination, where the antiemetic combination is a 5-HT3 antagonist and a NK-1 antagonist, for the preparation of medicaments consisting of a pharmaceutical composition comprising said antiemetic combination where the 5-HT3 antagonist and the NK-1 antagonist are each in an amount at least as high as or equal to the pediatric or adult dose approved for the prevention of chemotherapy-induced nausea and vomiting, in admixture with a pharmaceutical carrier, for preventing or curing the adverse effects of pyridostigmine in the pretreatment of OP poisoning. The invention also includes the use of an antiemetic combination, where the antiemetic combination is a 5-HT3 antagonist and a NK-1 antagonist for the preparation of medicaments consisting of a pharmaceutical composition comprising, said antiemetic combination where the 5-HT3 antagonist and the NK-1 antagonist are each in an amount higher or greater than the pediatric or adult dose approved for the prevention of chemotherapy-induced nausea and vomiting, in admixture with a pharmaceutical carrier, for preventing or curing the adverse effects of pyridostigmine in the pretreatment of OP poisoning.

As set forth above, the amount of the antiemetic, where the antiemetic is a 5-HT3 antagonist or a NK-1 antagonist, is at least as high as or equal to, the pediatric or adult dose approved for the prevention of chemotherapy-induced nausea and vomiting and may in the case of 5-HT3 antagonists be up to 10 times said dose, and in the case of NK-1 antagonists be up to 6 times said dose. Alternatively, the amount of the antiemetic, where the antiemetic is a 5-HT3 antagonist or a NK-1-antagonist, is higher or greater than the pediatric or adult dose approved for the prevention of chemotherapy-induced nausea and vomiting and may in the case of 5-HT3 antagonists be up to 10 times said dose, and in the case of NK-1 antagonists be up to 6 times said dose.

According to yet further embodiments, the invention provides pharmaceutical fixed-dose combinations consisting of a pharmaceutical composition comprising an antiemetic, where the antiemetic is a 5-HT3 antagonist or a NK-1 antagonist, in an amount that is at least as high as or equal to, the pediatric or adult dose approved for the prevention of chemotherapy-induced nausea and vomiting, as Component (a) and an effective dose of a pharmaceutically acceptable salt of pyridostigmine, neostigmine, rivastigmine, or physostigmine as Component (b), in admixture with a pharmaceutical carrier or vehicle. In alternative embodiments, the invention provides pharmaceutical fixed-dose combinations consisting of a pharmaceutical composition comprising an antiemetic, where the antiemetic is a 5-HT3 antagonist or a NK-1 antagonist, in an amount that is higher or greater than the pediatric or adult dose approved for the prevention of chemotherapy-induced nausea and vomiting, as Component (a) and an effective dose of a pharmaceutically acceptable salt of pyridostigmine, neostigmine, rivastigmine, or physostigmine as Component (b), in admixture with a pharmaceutical carrier or vehicle.

According to yet further embodiments, the invention provides pharmaceutical fixed-dose combinations consisting of a pharmaceutical composition comprising an antiemetic combination, where the antiemetic combination is a 5-HT3 antagonist and a NK-1 antagonist, where the 5-HT3 antagonist and the NK-1 antagonist are each in an amount that is at least as high as or equal to, the pediatric or adult dose approved for the prevention of chemotherapy-induced nausea and vomiting, as Component (a) and an effective dose of a pharmaceutically acceptable salt of pyridostigmine, neostigmine, rivastigmine, or physostigmine as Component (b), in admixture with a pharmaceutical carrier or vehicle. In alternative embodiments, the invention provides pharmaceutical fixed-dose combinations consisting of a pharmaceutical composition comprising an antiemetic combination, where the antiemetic combination is a 5-HT3 antagonist and a NK-1 antagonist, where the 5-HT3 antagonist and the NK-1 antagonist are each in an amount that is higher or greater than the pediatric or adult dose approved for the prevention of chemotherapy-induced nausea and vomiting, as Component (a) and an effective dose of a pharmaceutically acceptable salt of pyridostigmine, neostigmine, rivastigmine, or physostigmine as Component (b), in admixture with a pharmaceutical carrier or vehicle.

The dose of pyridostigmine IR normally as bromide per tablet will range from 30 mg to 90 mg, depending on safety and tolerability (per day the dose ranges from approx. 240 mg to 1080 mg). The dose of pyridostigmine Extended Release (ER) per tablet will range from 90 to 360 mg per tablet (per day the dose ranges from approx. 500 mg to 3000 mg). The dose of neostigmine, normally as bromide, in an IR tablet will range from 15 mg to 75 mg, depending on safety and tolerability. The dose of rivastigmine normally as tartrate in an IR tablet will range from 6 to 24 mg, in a daily patch the dose will range from 9.5 mg/day to 47.5 mg/day, depending on safety and tolerability. The dose of oral IR or sublingual physostigmine will range from 3.5 mg daily to 32 mg daily, given in divided doses every 2 hours. The dose of ER physostigmine will range from 9 mg to 15 mg administered every 4 hours. The dose of physostigmine administered IR will range from 0.5 mg to 2 mg administered every 20 min. The amount of physostigmine administered by TTS will range from 3 to 12 mg over 24 hours; the dose by intravenous bolus injection will range from 100 ug/kg to 300 ug/kg. An advantage of the intravenous route is that maximal inhibition in plasma (>78%) is reached in 2 minutes, allowing for very rapid protection against OP poisoning.

5-HT3 Antagonists

When the 5-HT3 antagonist is ondansetron, the dose per tablet in combination with pyridostigmine is from 4 mg to 8 mg (per day the dose ranges from 8 to 12 mg).

When the 5-HT3 antagonist is dolasetron, the dose per tablet in combination with pyridostigmine is from 100 mg to 200 mg.

Ondansetron may also be present in a slow-release oral composition, or in an intravenous preparation The 5-HT3 antagonist is preferably selected from the group consisting of 5-methyl-2-[(4-methyl-1H-imidazol-5-yl)methyl]-2,3,4,5-tetrahydro-1H-pyrido[4,3-b]indol-1-one (alosetron) and pharmaceutically acceptable salts and solvates thereof, especially its hydrochloride, disclosed in U.S. Pat. No. 5,360,800, which is herein incorporated by reference in its entirety; 6-chloro,3,4-dihydro-4-methyl-3-oxo-N-(quinuclidinyl)-2H-1,4-benzoxazine-8-carboxamide (azasetron) and pharmaceutically acceptable salts and solvates thereof, especially its hydrochloride, disclosed in U.S. Pat. No. 4,892,872, which is herein incorporated by reference in its entirety; [(1S,5R)-8-methyl-8-azabicyclo[3.2.1]octan-3-yl]3,5-dichlorobenzoate (bemesetron, CAS: 40796-97-2); (10R)-10-[(2-methyl-1H-imidazol-1-yl)methyl]-5,6,9,10-tetrahydro-4H-pyrido(3,2,1-jk)carbazol-11-one (cilansetron) and pharmaceutically acceptable salts and solvates thereof, especially its hydrochloride monohydrate, disclosed in U.S. Pat. No. 4,939,136, which is herein incorporated by reference in its entirety; (3R)-10-oxo-8-azatricyclo[5.3.1.03,8]undec-5-yl 1H-indole-3-carboxylate (dolasetron) and pharmaceutically acceptable salts and solvates thereof, especially its monomethanesulfonate monohydrate, disclosed in U.S. Pat. No. 4,906,755, which is herein incorporated by reference in its entirety; (+)—(R)-8,9-dihydro-10-methyl-7-[(5-methylimidazol-4-yl)methyl]pyrido[1,2-a]indol-6(7H)-one (fabesetron) and pharmaceutically acceptable salts and solvates thereof, especially its hydrochloride or maleate, disclosed in U.S. Pat. No. 5,141,945, which is herein incorporated by reference in its entirety; 1-methyl-N-((1R,3r,5S)-9-methyl-9-azabicyclo[3.3.1] nonan-3-yl)-1H-indazole-3-carboxamide (granisetron) and pharmaceutically acceptable salts and solvates thereof, especially its hydrochloride, disclosed in U.S. Pat. No. 4,886,808, which is herein incorporated by reference in its entirety; 2,3-dihydro-N-(8-methyl-8-azabicyclo[3.2.1]oct-3-yl)-2-oxo-1H-benzimidazole-1-carboxamide (itasetron) and pharmaceutically acceptable salts and solvates thereof, especially its hydrochloride, disclosed in U.S. Pat. No. 5,223,511, which is herein incorporated by reference in its entirety; 1-phenylmethyl-2-(1-piperazinyl)-1H-benzimidazole (lerisetron) and pharmaceutically acceptable salts and solvates thereof, specially its hydrochloride, disclosed in U.S. Pat. No. 5,256,665 and, in a transdermal preparation, in U.S. Pat. No. 6,136,807, the disclosures of which are herein incorporated by reference in their entirety; 6-fluoro-5-methyl-2-[(5-methyl-1H-imidazol-4-yl)methyl]-2,3,4,5-tetrahydro-1H-pyrido[4,3-b]indol-1-one (lurosetron, CAS 128486-54-4) and pharmaceutically acceptable salts and solvates thereof, especially its mesylate (GR 87442 N); (±) 1,2,3,9-tetrahydro-9-methyl-3-[(2-methyl-1H-imidazol-1-yl)methyl]-4H-carbazol-4-one (ondansetron) and pharmaceutically acceptable salts and solvates thereof, especially its hydrochloride dihydrate, disclosed in U.S. Pat. No. 4,695,578, which is herein incorporated by reference in its entirety; (3a5)-2-[(S)-1-azabicyclo[2.2.2]oct-3-yl]-2,3,3a,4,5,6-hexahydro-1-oxo-1H-benz[de]isoquinoline (palonosetron) and pharmaceutically acceptable salts and solvates thereof, especially its hydrochloride, disclosed in U.S. Pat. No. 5,202,333, which is herein incorporated by reference in its entirety; 1-methylindol-3-yl)-[(5R)-4,5,6,7-tetrahydro-3H-benzimidazol-5-yl]methanone (ramosetron) and pharmaceutically acceptable salts and solvates thereof, especially its fumarate, disclosed in U.S. Pat. No. 5,344,927, which is herein incorporated by reference in its entirety; endo-N-(8-methyl-8-azabicyclo[3.2.1]oct-3-yl)-2,3-dihydro-3,3-dimethyl-indole-1-carboxamide (3,3-dimethyl-N— 1αH,5αH-tropan-3α-yl-1-indolinecarboxamide, ricasetron, CAS 117086-68-7) and pharmaceutically acceptable salts and solvates thereof, especially its hydrochloride; the (3-endo)-8-methyl-8-azabicyclo[3.2.1]oct-3-yl ester of 1H-indole-3-carboxylic acid (3-tropanylindole-3-carboxylate, tropisetron) and pharmaceutically acceptable salts and solvates thereof, especially its hydrochloride, disclosed in U.S. Pat. No. 4,789,673, which is herein incorporated by reference in its entirety; and 5-chloro-2,2-dimethyl-N-(8-methyl-8-azabicyclo[3.2.1]oct-3-yl)-2,3-dihydro-1-benzofuran-7-carboxamide (zatosetron) and pharmaceutically acceptable salts and solvates thereof, especially its maleate, disclosed in U.S. Pat. No. 5,563,148, which is herein incorporated by reference in its entirety.

Antagonists of the 5-HT3 receptor that are approved for the prevention of chemotherapy-induced nausea and vomiting are particularly useful according to the present invention. In particular, azasetron hydrochloride, commercially available in 10-mg tablets; dolasetron monomethanesulfonate monohydrate (also referred to as dolasetron mesylate), commercially available in 200-mg maximal dose tablet; granisetron hydrochloride, commercially available in 2.24 mg maximal dose tablet; ondansetron hydrochloride dihydrate, commercially available in 10 mg maximal dose tablet; palonosetron hydrochloride, commercially available in 0.56 mg tablets; and tropisetron hydrochloride, commercially available in 5.64 mg capsules; are the preferred 5-HT antagonists.

NK-1 Antagonists

When the NK-1 antagonist is aprepitant, the dose per tablet, in combination with pyridostigmine, is from 80 mg to 120 mg of aprepitant.

When the NK-1 antagonist is aprepitant, the dose per tablet in combination with pyridostigmine IR is 80 mg to 120 mg of aprepitant. Likewise, when the NK-1 antagonist is aprepitant, the dose per tablet in combination with pyridostigmine ER is 80 mg to 120 mg of aprepitant.

The NK-1 antagonist Component (a) preferably includes, but is not limited to:

5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one (aprepitant); described in U.S. Pat. No. 5,719,147, and in a liquid oral formulation, in US 2017/0035774, the disclosures of which are incorporated herein in their entirety by reference;

[3-1R2R,3S)-2-[(1R)-1-[3,5-bis(trifluoromethyl)phenyl]ethoxy]-3-(4-fluorophenyl)morpholin-4-yl]methyl}-5-oxo-2H-1,2,4-triazol-1-yl]phosphonic acid(fosaprepitant), disclosed, for example as meglumine salt in U.S. Pat. No. 5,691,336 and as di(cyclohexylamine) salt in US 2016/355533, the disclosures of which are incorporated herein in their entirety by reference;

(2S,4S)-4-(4-Acetyl-1-piperazinyl)-N-[(1R)-1-[3,5-bis(trifluoromethyl)phenyl]ethyl]-2-(4-fluoro-2-methylphenyl)-N-methyl-1-piperidinecarboxamide (casopitant) described in U.S. Pat. No. 7,294,630, the disclosure of which is incorporated herein in its entirety by reference;

(2S,3S)—N-(5-tert-Butyl-2-methoxybenzyl)-2-(diphenylmethyl)-1-azabicyclo[2.2.2]octan-3-amine (maropitant);

(2S,3S)-2-Diphenylmethyl-3-[(5-isopropyl-2-methoxybenzyl)amino]quinuclidine (eziopitant), disclosed by Evangelista S (2001). "Eziopitant. Pfizer"; Current Opinion in Investigational Drugs: 2 (10): 1441-3; reviewed in Drugs: the Investigational Drugs Journal 6 (8): 758-72, the disclosure of which is incorporated herein in its entirety by reference;

N-[(2R)-1-[Acetyl-[(2-methoxyphenyl)methyl]amino]-3-(1H-indol-3-yl)propan-2-yl]-2-(4-piperidin-1-ylpiperidin-1-yl)acetamide (lanepitant);

2-[3,5-bis(trifluoromethyl)phenyl]-N,2-dimethyl-N-[4-(2-methylphenyl)-6-(4-methyl-1-piperazinyl)-3-pyridinyl]propanamide (netupitant) described in U.S. Pat. Nos. 6,297,375, 6,719,996 and 6,593,472, the disclosures of which are incorporated herein in their entirety by reference;

(2R,4S)-4-[(8aS)-6-oxo-1,3,4,7,8,8a-hexahydropyrrolo[1,2-a]pyrazin-2-yl]-N-[(1R)-1-[3,5-bis(trifluoromethyl)phenyl]ethyl]-2-(4-fluoro-2-methylphenyl)-N-methylpiperidine-1-carboxamide maleate (orvepitant), described in U.S. Pat. Nos. 7,652,012 and 8,309,553, the disclosures of which are incorporated herein in their entirety by reference;

(5S,8S)-8-({(1R)-1-[3,5-bis(trifluoromethyl)phenyl]ethoxy}methyl)-8-phenyl-1,7-diazaspiro[4.5]decan-2-one (rolapitant), described in U.S. Pat. No. 7,049,320 and, for an injectable form thereof, in U.S. Pat. No. 9,101,615, the disclosures of which are incorporated herein in their entirety by reference;

3-((3aR,4R,5S,7a5)-5-[(1R)-1-[3,5-bis(trifluoromethylphenyl]ethoxy]-4-(4-fluorophenyl)-1,3,3a,4,5,6,7,7a-octahydroisoindol-2-ylcyclopent-2-en-1-one (serlopitant) described in U.S. Pat. Nos. 7,544,815 and 7,217,731, the disclosures of which are incorporated herein in their entirety by reference;

2-(S)-(4-Fluoro-2-methyl-phenyl)-piperazine-1-carboxylic acid [1-(R)-(3,5-bis-trifluoromethyl-phenyl)-ethyl]-methyl-amide (vestipitant), described in WO 2001/25219 and, in intravenous formulation having a reduced tendency to cause hemolysis, in WO 2012/175434, the disclosures of which are incorporated herein in their entirety by reference; and (2S,3S)—N-[(2-methoxy-5-]5-(trifluoromethyl)tetrazol-1-yl[phenylmethyl]-2-phenylpiperidin-3-amine (vofopitant), disclosed by Gardner C J et al. Regul Pept. 1996 Aug. 27; 65(1):45-53. the disclosure of which is incorporated herein in its entirety by reference.

Antagonists of the NK-1 receptor that are approved for the prevention or treatment of postoperative nausea and vomiting or for the prevention of chemotherapy-induced nausea and vomiting are particularly useful according to the present invention. In particular, aprepitant is commercially available (Emend®) in capsules containing 40 mg, 80 mg, or 125 mg aprepitant or, as fosaprepitant dimeglumine (Emend® Injection), in vials containing 115 mg or 150 mg fosaprepitant; rolapitant is available (Varubi®) in 90-mg tablets; and netupitant is available (Akynzeo®) in a fixed-dose combination in capsules containing 300 mg of netupitant and 0.5 mg of the 5-HT3 antagonist palonosetron (as hydrochloride), herein below referred to as "netupitant300 mg/palonosetron0.5 mg". Each of these preparations is a particularly advantageous NK-1 antagonist Component (a) for the combination with ChEIs such as pyridostigmine, neostigmine, rivastigmine, or physostigmine and the pharmaceutically acceptable salts and solvates thereof as Component (b) according to the present invention.

Preferably, for said use in the prevention or treatment of OP in a subject, said NK1-antagonist Component (a) is aprepitant at a daily oral dose of from 80 mg to 120 mg; rolapitant, at a daily oral dose of from 30 mg to 270 mg or netupitant 300 mg/palonosetron0.5 mg, orally administered once a day, each in combination with a ChEI such as pyridostigmine, or rivastigmine, or neostigmine, or physostigmine, or a pharmaceutically acceptable salt thereof as Component (b) at a daily dose equivalent to up to 4.7 times higher than the maximum recommended dose for the treatment of Alzheimer's disease.

In carrying out the method of the present invention, the daily dose of the antiemetic, where the antiemetic is a 5-HT3 antagonist or a NK-1 antagonist, is at least as high as or equal to the dose used to prevent nausea and vomiting in pediatric or adult patients undergoing cancer chemotherapy according to the current protocols for said treatment. In alternative embodiments, in carrying out the method of the present invention, the daily dose of the antiemetic, where the antiemetic is a 5-HT3 antagonist or a NK-1 antagonist, is higher or greater than the dose used to prevent nausea and vomiting in pediatric or adult patients undergoing cancer chemotherapy according to the current protocols for said treatment.

For use in the treatment of OP poisoning in combination with pyridostigmine, an antiemetic, where the antiemetic is a 5-HT3 antagonist or a NK-1 antagonist, is formulated in a pharmaceutical composition, wherein said antiemetic is in admixture with a pharmaceutical carrier or vehicle.

For use in the treatment of OP poisoning in combination with pyridostigmine, an antiemetic combination, where the antiemetic combination is a 5-HT3 antagonist and a NK-1 antagonist, is formulated in a pharmaceutical composition, wherein said antiemetic combination is in admixture with a pharmaceutical carrier or vehicle.

The composition of this invention may be provided as a pharmaceutical composition comprising a pharmaceutically effective amount of at least one antiemetic, where the antiemetic is a 5-HT3 antagonist and/or a NK-1 antagonist, or pharmaceutically acceptable salt thereof, and a ChEI as described herein.

Thus, according to one aspect, the present invention provides pharmaceutical compositions including, as one of the active ingredients, at least one pharmacologically active amount of an antiemetic, where the antiemetic is a 5-HT3 antagonist and/or a NK-1 antagonist, as shown above or of one of its pharmaceutically acceptable salts, in mixture with a pharmaceutical carrier or vehicle.

In the pharmaceutical compositions of the present invention for oral, subcutaneous, intravenous, transdermal or topical administration, the active ingredient is preferably administered in the form of dosage units, in mixture with the classic pharmaceutical carriers or vehicles.

A suitable dosage amount of the pharmaceutical composition of the present invention can vary depending on pharmaceutical formulation methods, administration methods, the patient's age, weight, sex, health condition of the patient, diet, administration time, administration route, an excretion rate and sensitivity for a used pharmaceutical composition. For instance, the dosage of the antiemetic, where the antiemetic is a 5-HT3 antagonist and/or a NK-1 antagonist, may be determined in accordance with the respective potency of each antagonist and the age of the patient, and administered from one to several times a day by intravenous, subcutaneous, oral, or transcutaneous administration. For 5-HT3 antagonists, said dosage will range from 1 µg to 300 mg.

The pharmaceutical compositions of the present invention are formulated with classic pharmaceutical excipients suitable for the different ways of administration. Particularly advantageous are the formulations in the form of tablets, multi-score tablets, coated tables, orally disintegrating tablets, extended release tablets, hard or soft capsules, extended-release capsules, patches for transdermal administration, liquid oral solutions, syrups or suspensions in a predetermined unit form, and vials for intravenous, intramuscular, or subcutaneous administration.

The pharmaceutical composition of this invention includes a pharmaceutically acceptable carrier besides an antiemetic, where the antiemetic is a 5-HT3 antagonist and/or a NK-1 antagonist, or pharmaceutically acceptable salt thereof as the active ingredient. The pharmaceutically acceptable carrier contained in the pharmaceutical composition of the present invention, which is commonly used in pharmaceutical formulations. Suitable pharmaceutically acceptable carriers and formulations can be found in Remington's Pharmaceutical Sciences ($22^{nd}$ ed., 2013), which is herein incorporated by reference in its entirety.

According to the conventional techniques known to those skilled in the art, the pharmaceutical composition according to the present invention may be formulated with pharmaceutically acceptable carrier and/or vehicle as described above, to provide dosage forms including a unit dose form and a multi-dose form. Non-limiting examples of the formulations include, but not limited to, a solution, a suspension or an emulsion in oil or aqueous medium, an elixir, a powder, a granule, a tablet and a capsule.

The invention further relates to a transdermal therapeutic system comprising an antiemetic, where the antiemetic is a 5-HT3 antagonist or a NK-1 antagonist, or pharmaceutically acceptable salt thereof, and an ChEI as described herein. Alternatively, the invention relates to a transdermal therapeutic system comprising an antiemetic combination, where the antiemetic combination is a 5-HT3 antagonist and a NK-1 antagonist, or pharmaceutically acceptable salt thereof, and an ChEI as described herein. In particular, the transdermal therapeutic system involves delivering said antiemetic or said antiemetic combination with a high-dose of an ChEI and in particular, an AChEI in some preferred embodiments, via transdermal formulation(s) and transdermal patches incorporating such formulations. The present invention also relates to transdermal drug formulations, transdermal patches incorporating such formulations, as well as associated methods of use for improving the protection of humans and other mammals at risk of being exposed to OP compounds, and methods for treating, preventing, or alleviating an effect of an OP compound in humans and other mammals exposed to an OP compound. The formulations of the present invention can be incorporated into patches for transdermal administration. For instance, a transdermal patch for transdermal delivery of said antiemetic and a transdermal patch for transdermal delivery of an acetylcholine esterase inhibitor. Alternatively, the transdermal patch for transdermal delivery of said antiemetic is combined with an orally administered ChEI, or, a transdermal patch for transdermal delivery of ChEI is combined with oral administration of said antiemetic.

In yet another embodiment, the dose of the ChEI may be higher than the maximum recommended daily dose, in particular from 1.1 to 10 times higher than a recommended maximal daily dose level; or, the acetyl choline esterase inhibitor may be higher than the maximal tolerated dose, in particular, from 1.1 to 10 times higher than the maximal tolerated dose. The "maximum tolerated dose," "maximal tolerated dose" or "MTD" refers to, and is defined as the highest dose of a drug or treatment that does not cause unacceptable side effects. The maximum tolerated dose is determined in clinical trials by testing increasing doses on different groups of people until the highest dose with acceptable side effects is found Thus, for example, using 5-HT3 antagonists, a pharmaceutical composition according to the present invention to be chronically or recurrently administered in combination with pyridostigmine may comprise azasetron hydrochloride, in an amount of from 5 mg to 10 mg to be administered at a daily dose of from 15 mg to 40 mg; dolasetron mesylate, in an amount of from 25 mg to 200 mg to be administered at a daily dose of from 75 mg to 800 mg; granisetron hydrochloride, in an amount equivalent to from 0.5 mg to 2 mg granisetron base, to be administered at a daily dose of from 1.5 mg to 8 mg; ondansetron hydrochloride dihydrate, in an amount equivalent to from 2 mg to 8 mg ondansetron base, to be administered at a daily dose of from 8 to 12 mg; palonosetron hydrochloride, in an amount equivalent to from 0.25 mg to 0.5 mg palonosetron base, to be administered at a daily dose of from 0.75 to 2 mg; tropisetron hydrochloride, in an amount equivalent to from 2.5 mg to 5 mg tropisetron base, to be administered at a daily dose of from 7.5 to 20 mg.

Similarly, for NK-1 antagonists, a pharmaceutical composition according to the present invention to be chronically or recurrently administered in combination with pyridostigmine may comprise antagonists of the NK-1 receptor that are approved for the prevention or treatment of postoperative nausea and vomiting or for the prevention of chemotherapy-induced nausea and vomiting. Thus, for example, a pharmaceutical composition according to the present invention to be chronically or recurrently administered in combination with pyridostigmine may comprise aprepitant at a daily oral dose of from 80 mg to 120 mg; rolapitant, at a daily oral dose of from 30 mg to 270 mg or netupitant 300 mg/palonosetron 0.5 mg, orally administered once a day.

In the case of pediatric or obese patients, the daily dose may be determined based on body weight. Thus, for example, for 5-HT3 antagonists, azasetron hydrochloride may be administered at a daily dose of 0.4-0.5 mg/kg, dolasetron mesylate may be administered at a daily dose of 9-9.5 mg/kg, granisetron hydrochloride may be administered at a daily dose of 0.09-0.11 mg/kg, ondansetron hydrochloride dihydrate may be administered at a daily dose of 0.114-0.171 mg/kg, palonosetron hydrochloride may be administered at a daily dose of 0.03 mg/kg and tropisetron hydrochloride may be administered at a daily dose of 0.5-0.6 mg/kg. Similarly, for example, for NK-1 antagonists, aprepitant may be administered at a daily dose of 1.14-1.71 mg/kg daily, and rolapitant may be administered at a daily dose of 2-18 mg/kg.

According to another aspect of the present invention, the pharmaceutical composition comprising an antiemetic may contain another active ingredient, in particular, a pharmaceutically acceptable salt of pyridostigmine, co-formulated with said. NK-1 antagonist, in admixture with a pharmaceutical carrier.

EXAMPLES

Example 1

The ability of a 5-HT3 antagonist for preventing the adverse effects of pyridostigmine bromide in humans was tested.

A Phase I study was conducted in human subjects receiving an oral dose of pyridostigmine bromide with or without an oral dose of ondansetron hydrochloride dihydrate, as a representative 5-HT3 antagonist. The study was a single center, single-blind, placebo-controlled study.

The objective of the study was to demonstrate the safe attenuation by ondansetron, of gastro-intestinal side effects of pyridostigmine given in doses demonstrated to be effective for the treatment of OP poisoning. To be enrolled in the study, participants (aged 18 to 60 years of age) were required to be in good health, to refrain from consuming xanthine, quinine and caffeine containing beverages, and to refrain from prolonged intensive physical exercise during the study conduct. All subjects signed an informed consent form indicating that they understood the purpose of, and the procedures required for the study, and that they were willing to participate in the study and comply with the study procedures and restrictions. The key criteria for exclusion of a subject from enrollment in the study were as follows:

any clinically relevant acute or chronic disease which could interfere with the subjects' safety during the trial, expose them to undue risk, or interfere with the study objectives;
history or presence of gastrointestinal, hepatic, or renal disease or other condition known to interfere with the absorption, distribution, metabolism or excretion of drugs;
history of substance abuse, known drug addiction, or positive test for drugs of abuse or alcohol;
history of drug or other significant allergy;
ECG changes including QT interval prolongation and congenital long QT syndrome. Electrolyte abnormalities (e.g., hypokalemia or hypomagnesemia), congestive heart failure, bradyarrhythmias or other conditions that lead to QT prolongation;
treatment with centrally active drugs or those affecting peripheral cholinergic transmission within 3 months of study entry;
smokers (except subjects who stopped smoking 1 year or more before enrollment in the Study);
excessive daily consumption of xanthines containing drinks (i.e. >500 mg/day of caffeine);
intake of an investigational drug within 30 days of study entry.

Following enrollment in the study, participants received oral doses of pyridostigmine, with the total dose per day being increased on a daily basis. Once a subject had reached his/her first intolerable daily dose, dosing was discontinued for wash-out. First intolerable dose was defined as an amount inducing at least one of the following:

(a) one episode of vomiting; or
(b) two episodes of retching; or
(c) one episode of severe nausea; or
(d) one episode of moderate diarrhea (Grade 2).

Following a wash-out for 2 to 7 days, participants then received their first intolerable dose of pyridostigmine plus a single oral dose of ondansetron hydrochloride dihydrate (10 mg, equivalent to 8 mg ondansetron base) or ondansetron placebo, and the dose of pyridostigmine was again titrated up on a daily basis to a second intolerable dose (FID-2). The highest tolerated daily dose of pyridostigmine when administered with ondansetron is defined as the tolerated dose achieved just before FID-2).

On each study day, subjects were followed up for up to 8 hours for AEs, vital signs, ECGs, and a laboratory panel at screening and at the end of the study.

Results showed that the co-administration of ondansetron with pyridostigmine at FID attenuated gastro-intestinal AEs reported with pyridostigmine alone at FID. Furthermore, in the presence of ondansetron, higher doses of pyridostigmine could be tolerably given, with the highest tolerated daily dose generally exceeding the recommended dose for the treatment of OP poisoning.

In conclusion, the co-administration of oral high dose ondansetron with pyridostigmine prevented the occurrence of gastro-intestinal AEs when pyridostigmine was given in doses as high as or higher than the recommended efficacious dose for the treatment of OP poisoning.

Example 2

The ability of a NK-1 antagonist for preventing the adverse effects of pyridostigmine bromide in humans was tested.

A Phase I study was conducted in human subjects receiving a single oral dose of pyridostigmine bromide with or without a single oral dose of aprepitant, as a representative NK-1 receptor antagonist. The study was a single center, single-blind, placebo-controlled study.

The objective of the study was to demonstrate the safe attenuation by aprepitant, of gastro-intestinal side effects of pyridostigmine given in doses demonstrated to be effective for the treatment of OP poisoning. To be enrolled in the study, participants (aged 18 to 60 years of age) were required to be in good health, to refrain from consuming xanthine, quinine and caffeine containing beverages, and to refrain from prolonged intensive physical exercise during the study conduct. All subjects signed an informed consent form indicating that they understood the purpose of, and the procedures required for the study, and that they were willing to participate in the study and comply with the study procedures and restrictions. The key criteria for exclusion of a subject from enrollment in the study were as follows:
- any clinically relevant acute or chronic disease which could interfere with the subjects' safety during the trial, expose them to undue risk, or interfere with the study objectives;
- history or presence of gastrointestinal, hepatic, or renal disease or other condition known to interfere with the absorption, distribution, metabolism or excretion of drugs;
- history of substance abuse, known drug addiction, or positive test for drugs of abuse or alcohol;
- history of drug or other significant allergy;
- ECG changes including QT interval prolongation and congenital long QT syndrome. Electrolyte abnormalities (e.g., hypokalemia or hypomagnesemia), congestive heart failure, bradyarrhythmias or other conditions that lead to QT prolongation;
- treatment with centrally active drugs or those affecting peripheral cholinergic transmission within 3 months of study entry;
- smokers (except subjects who stopped smoking 1 year or more before enrollment in the Study);
- excessive daily consumption of xanthines containing drinks (i.e. >500 mg/day of caffeine);
- intake of an investigational drug within 30 days of study entry.

Following enrollment in the study, participants received single increasing oral doses of pyridostigmine, given once daily in the morning. Once a subject had reached his/her first intolerable dose, upward dose escalation was discontinued. First intolerable dose was defined as an amount inducing at least one of the following:
- (a) one episode of vomiting; or
- (b) two episodes of retching; or
- (c) one episode of severe nausea; or
- (d) one episode of moderate diarrhea (Grade 2).

Following a wash-out, participants then entered Period 2 of the study during which they received single increasing doses of oral pyridostigmine given daily in the morning with a single dose of aprepitant (80 mg to 120 mg) until they reached an intolerable dose of pyridostigmine as defined above (FID-2)

On each study day, subjects were followed up for up to 8 hours for AEs, vital signs, ECGs, and a laboratory panel at screening and at the end of the study.

Results showed that the co-administration of aprepitant with pyridostigmine at FID attenuated gastro-intestinal AEs reported with pyridostigmine alone at FID. Furthermore, in the presence of aprepitant, higher doses of pyridostigmine could be tolerably given, with the highest tolerated daily dose generally exceeding the recommended dose for the treatment of OP poisoning.

In conclusion, the co-administration of oral aprepitant with pyridostigmine prevented the occurrence of gastro-intestinal AEs given in doses as high as or higher than (up to 6 times) the recommended efficacious dose for the treatment of OP poisoning.

REFERENCES

Albuquerque et A 2006: Albuquerque EX1, Pereira. E F, Aracava Y, Fawcett W P, Oliveira M, Randall W R, Hamilton T A, Kan R K, Romano J A Jr, Adler M. Effective countermeasure against poisoning by organophosphorus insecticides and nerve agents. Proc Natl Acad Sci USA. 2006 Aug. 29; 103(35):13220-5. Epub 2006 Aug. 16.

Bartolucci et al. 2012: Bartolucci Cl, Stojan J, Yu Q S, Greig N H, Lamba D. Kinetics of Torpedo *californica* acetylcholinesterase inhibition by bisnorcymserine and crystal structure of the complex with its leaving group. Biochem J. 2012 Jun. 1; 444(2):269-77. doi: 10.1042/BJ20111675.

Buckley et al. 2004: Buckley N, Karalliedde L, Dawson A, Senanayake N, and Eddleston M. Where is the Evidence for Treatments used in Pesticide Poisoning?—Is Clinical Toxicology Fiddling while the Developing World Burns? J Toxicol Clin Toxicol. 2004; 42(1): 113-116.

Coupland and Leins, 2005: Coupland R, Leins K R. Science and prohibited weapons. Science 2005; June 24; 308 (5730):1841.

Darreh-Shori and Soininen, 2010: Darreh-Shori T1, Soininen H. Effects of cholinesterase inhibitors on the activities and protein levels of cholinesterases in the cerebrospinal fluid of patients with Alzheimer's disease: a review of recent clinical studies. Curr Alzheimer Res. 2010 February; 7(1):67-73.

Doctor et al. 1991: Doctor B P, Raveh L, Wolfe A D, Maxwell D M, Ashani Y. Enzymes as pretreatment drugs for organophosphate toxicity. Neurosci Biobehav Rev. 1991 Spring; 15(1):123-8.

Karalliedde and Snanayake, 2005: Karalliedde L and Senanayake N. Organophosphorus insecticide poisoning. Br J Anaesth. 1989 December; 63(6):736-50.

Pohanka, 2014: Pohanka M. Inhibitors of Acetylcholinesterase and Butyrylcholinesterase Meet Immunity Int. J. Mol. Sci. 2014, 15, 9809-9825.

Tayeb et al. 2012: Tayeb H O, Yang Ft), Price B H, Tarazi F I. Pharmacotherapies for Alzheimer's disease: beyond cholinesterase inhibitors. Pharmacol Ther. 2012 April; 134(1):8-25. doi: 10.1016/j.pharmthera.2011.12.002. Epub 2011 December 16.

Triggle et al. 1998: Triggle D J, Mitchell J M, Filer R. The Pharmacology of Physostigmine. CNS Drug Reviews 1998; 4, (2), pp. 87-136.

The invention claimed is:

1. A method for protecting against toxicity from a nerve agent in a subject at risk of exposure to a nerve agent, or preventing or alleviating/reducing toxicity from a nerve agent in a subject exposed to a nerve agent, comprising administering to said subject one or more of an antiemetic selected from the group consisting of a 5-HT3 antagonist and an NK-1 antagonist in combination with an effective daily dose of a choline esterase inhibitor or pharmaceutically acceptable salt thereof, wherein the choline esterase inhibitor is selected from the group consisting of pyridostigmine or a pharmaceutically acceptable salt thereof, neostigmine or a pharmaceutically acceptable salt thereof, physostigmine or a pharmaceutically acceptable salt thereof, and rivastigmine or a pharmaceutically acceptable salt thereof,
  wherein the 5-HT3 antagonist is in an amount up to 10 times higher than a pediatric or adult dose approved for the prevention of chemotherapy-induced nausea and vomiting, and
  wherein the NK-1 antagonist is in an amount up to 6 times higher than a pediatric or adult dose approved for the prevention of chemotherapy-induced nausea and vomiting.

2. The method of claim 1, wherein the choline esterase inhibitor is pyridostigmine or a pharmaceutically acceptable salt thereof.

3. The method of claim 1, wherein the choline esterase inhibitor is neostigmine or a pharmaceutically acceptable salt thereof.

4. The method of claim 1, wherein the choline esterase inhibitor is physostigmine or a pharmaceutically acceptable salt thereof.

5. The method of claim 1, wherein the choline esterase inhibitor is rivastigmine or a pharmaceutically acceptable salt thereof.

6. The method of claim 1, wherein said antiemetic is an NK-1 antagonist selected from the group consisting of fosaprepitant, casopitant, aprepitant, rolapitant, maropitant, eziopitant, lanepitant, netupitant, orvepitant, serlopitant, vestipitant, vofopitant, and pharmaceutically acceptable salts or solvates thereof.

7. The method of claim 6, wherein said NK-1 antagonist is aprepitant or a pharmaceutically acceptable salt or solvate thereof.

8. The method of claim 6, wherein said NK-1 antagonist is rolapitant or a pharmaceutically acceptable salt or solvate thereof.

9. The method of claim 1, wherein said antiemetic is ondansetron or a pharmaceutically acceptable salt or solvate thereof.

10. The method of claim 2, wherein said antiemetic is ondansetron or a pharmaceutically acceptable salt or solvate thereof.

11. A pharmaceutical composition comprising an antiemetic and an effective daily dose of a choline esterase inhibitor, wherein the choline esterase inhibitor is selected from the group consisting of pyridostigmine or a pharmaceutically acceptable salt thereof, neostigmine or a pharmaceutically acceptable salt thereof, physostigmine or a pharmaceutically acceptable salt thereof, and rivastigmine or a pharmaceutically acceptable salt thereof,
   wherein the antiemetic is a 5-HT3 antagonist and/or an NK-1 antagonist,
   wherein the 5-HT3 antagonist is in an amount up to 10 times higher than a pediatric or adult dose approved for the prevention of chemotherapy-induced nausea and vomiting, and
   wherein the NK-1 antagonist is in an amount up to 6 times higher than a pediatric or adult dose approved for the prevention of chemotherapy-induced nausea and vomiting.

12. The pharmaceutical composition of claim 11, wherein the antiemetic is a 5-HT3 antagonist.

13. The pharmaceutical composition of claim 11, wherein the antiemetic is an NK-1 antagonist.

14. The method of claim 2, wherein pyridostigmine or a pharmaceutically acceptable salt thereof is administered at a daily dose of from 240 mg to 1080 mg of IR pyridostigmine or from 500 mg to 3000 mg of ER pyridostigmine.

15. The method of claim 4, wherein physostigmine or a pharmaceutically acceptable salt thereof is administered at a daily dose of from 3.5 mg daily to 32 mg of IR physostigmine or from 9 mg to 15 mg of ER physostigmine.

16. The pharmaceutical composition of claim 11, wherein the choline esterase inhibitor is pyridostigmine or a pharmaceutically acceptable salt thereof at an effective daily dose of from 240 mg to 1080 mg of IR pyridostigmine or from 500 mg to 3000 mg of ER pyridostigmine.

17. The pharmaceutical composition of claim 11, wherein the choline esterase inhibitor is physostigmine or a pharmaceutically acceptable salt thereof at an effective daily dose of from 3.5 mg daily to 32 mg of IR physostigmine or from 9 mg to 15 mg of ER physostigmine.

18. The pharmaceutical composition of claim 11, wherein the choline esterase inhibitor is neostigmine or a pharmaceutically acceptable salt thereof.

19. The method of claim 14, wherein the antiemetic is ondansetron administered at a daily dose of from 8 mg to 12 mg or aprepitant administered at a daily dose of from 80 mg to 120 mg.

20. The method of claim 15, wherein the antiemetic is ondansetron administered at a daily dose of from 8 mg to 12 mg or aprepitant administered at a daily dose of from 80 mg to 120 mg.

21. The method of claim 2, wherein the antiemetic is ondansetron administered at a daily dose of from 8 mg to 12 mg or aprepitant administered at a daily dose of from 80 mg to 120 mg.

22. The method of claim 1, wherein the nerve agent is an organophosphorus compound.

23. The pharmaceutical composition of claim 11, wherein a dose of said 5-HT3-antagonist is higher than an effective daily dose of 5HT3-antagonist and a dose of said NK-1 antagonist is higher than an effective daily dose of NK-1 antagonist.

* * * * *